(12) United States Patent
Close et al.

(10) Patent No.: US 6,532,380 B1
(45) Date of Patent: Mar. 11, 2003

(54) IMAGE GUIDANCE FOR CORONARY STENT DEPLOYMENT

(75) Inventors: Robert A. Close, Manhattan Beach; James S. Whiting; Craig K. Abbey, both of Los Angeles, all of CA (US)

(73) Assignee: Cedars Sinai Medical Center, Los Angeles, CA (US)

( * ) Notice: Subject to any disclaimer, the term of this patent is extended or adjusted under 35 U.S.C. 154(b) by 195 days.

(21) Appl. No.: 09/608,392

(22) Filed: Jun. 30, 2000

(51) Int. Cl.$^7$ .................................................. A61B 6/00
(52) U.S. Cl. ........................ 600/431; 382/130; 382/128; 600/407; 600/420
(58) Field of Search ............................... 600/407, 431, 600/420; 382/130, 128

(56) References Cited

U.S. PATENT DOCUMENTS 6,301,498 B1 * 10/2001 Greenberg et al. ........... 600/425
6,385,245 B1 * 5/2002 De Haan et al. ......... 375/240.16

OTHER PUBLICATIONS

R A Close and J S Whiting, "Comments on 'Retrospective Motion Correction in Digital Subtraction Angiography: A Review", IEEE Trans Med Imaging, vol. 18, No. 6, p. 556, Jun. 1999.*

J Y A Wang and E H Adelson, "Representing Moving Image with Layers", IEEE Trans Image Processing, vol. 3, No. 5, p. 625–638, Sep. 1994.*

T Saito, T. Komatsu, and Y Akimoto "Global Motion Segmentation for Mid–level Representation of Moving Images", IEEE, pp. 402–405, 1995.*

L Torres, D Garcia, and A. Mates, "A Robust Motion Estimation and Segmentation Approach to Represent Moving Images with Layers", IEEE, pp. 2981–2984, 1997.*

J Nam and A H Tewfik, "Progressive Resolution Motion Indexing of Video Object", IEEE, pp. 3701–3704, 1998.*

Y. Rozenman et al., "Quantitive videodensitometric technique for verification of optimal coronary stent implantation," *International Journal of Medical Informatics*, 51:51–57 (1998).

Erik H. W. Meijering et al., "Retrospective Motion Correction in Digital Subtraction Angiography: A Review," IEEE Transactions on Medical Imaging, vol. 18, No. 1, pp. 2–21, (Jan. 1999).

* cited by examiner

*Primary Examiner*—Marvin M. Lateef
*Assistant Examiner*—Runa S. Qaderi

(57) ABSTRACT

A method for image guidance of coronary stent deployment using radiopaque markers and the image processing technique of moving layer decomposition. The radiopaque markers are attached to guidewires or delivery balloons that are used to place the stent and co-moves with the coronary vessel. A series of fluoroscopic images are taken during the stent placement and are used to generate layer images which represent different structures in the angiograms, such as the stent and guidewires, background structures, etc. The clearly visible images of the markers are used in the layer decomposition. Although stents are less radiopaque than the markers, visibility of previously deployed stents is also enhanced in the layer images. The layer images are used to guide placement of multiple stents to prevent overlap or gaps between the stents. After stent expansion, angiographic images are acquired of the lumen filled with liquid contrast agent. Layer decomposition is applied to these images in order to visually or quantitatively determine the lumen narrowing (or broadening) in the stented region.

20 Claims, 2 Drawing Sheets

IMAGE GUIDANCE FOR CORONARY STENT DEPLOYMENT

BACKGROUND OF THE INVENTION

1. Field of the Invention

This invention relates to coronary stent deployment, and in particular, to improved image guidance in coronary stent deployment.

2. Description of the Related Art

Increasing numbers of percutaneous transluminal coronary angioplasty (PTCA) are being performed in the United States. However, after PTCA, restenosis of the dilated segment occurs in a large percentage of patients and results from elastic recoil, neointimal formation and vascular contraction. PTCA followed by coronary stent placement provides a luminal scaffolding that virtually eliminates recoil and remodeling, and has been shown to significantly reduce the likelihood of restenosis. Currently, a vast majority of patients receive stents after angioplasty. In such procedures, cardiologists frequently deploy multiple adjacent stents in an artery to treat extended lesions or dissections. Since it is important to accurately align the stent ends, the cardiologist must adjust the position of the catheter head relative to a previously deployed stent. This requires that the first stent and the catheter head be visualized well enough that their relative stent positions can be accurately determined. This has not been possible in conventional coronary stent deployment techniques. As a result, a subsequently placed stent often cannot be placed precisely in relation to a previously placed stent, resulting in either an overlap or a gap between the two stents. Gaps between stents are significant because of the risk of residual dissections and restenosis. Overlap of stents increases the risk of restenosis due to increased vessel injury during deployment. In addition, studies with intravascular ultrasounds (IVUS) imaging of deployed stents revealed that a high percentage of stents may be insufficiently dilated despite an apparently angiographically successful deployment.

Deployed stents may be evaluated using intravascular ultrasounds (IVUS) imaging technique (S. Nakamura et al., "Intracoronary ultrasound observations during stent implantation," *Circ.*, 89, pp. 2026–2034, 1994). IVUS can accurately define the anatomy of the vessel and the stent within the vessel and is considered the gold standard for defining the results of stent implantation. But such assessment is time-consuming and expensive, and is not useful for visualizing previously deployed stents during the placement of multiple stents because the ultrasound probe cannot be inserted along with the delivery balloon and stent. Moreover, the IVUS device is invasive and may increase patient risk. IVUS may also physically compromise the integrity of the deployment of certain stent types. An alternative method for evaluating stent expansion is coronary pressure measurement (C. E. Hanekamp et al., "Comparison of quantitative coronary angiography, intravascular ultrasound, and coronary pressure measurement to assess optimum stent deployment," *Circ.*, 99(8), pp. 1015–1021, 1999). Other alternative methods use medical imaging devices to evaluate stent implantation. One reference describes a videodensitometric analysis, in which density profiles are constructed and compared with a theoretic profile of a normal artery (Y. Rozenman et al., "Quantitative videodensitometric technique for verification of optimal coronary stent implantation," *International Journal of Medical Informatics*, 51(1), pp. 51–57, 1998). However, such measurements are typically imprecise, as evidenced in the Rozenman study by the weak correlation of only R=0.74 between the videodensitometric and IVUS measurements of stenosis.

Most coronary stents are insufficiently radiopaque and are difficult to visualize in x-ray angiograms. Thus, in evaluation techniques using medical imaging devices, it is desirable to increase the visibility of the stents. For example, the stents may be coated with radiopaque material such as gold to increase their visibility. Experimental studies with gold plated stents show results with less thrombogeneity of the stents, but clinical comparison of stainless steel stents and gold-plated stents show significantly increased restenosis rates with gold plating (A. Schomig et al., "Randomized comparison of gold-plated steel stent with conventional steel stent: Results of the angiographic follow-up," *Journal of the American College of Cardiology*, 33(2), pp. 95A, 1999). Stents and guidewires having radiopaque markers attached thereto have been described in numerous references, examples including Frantzen, U.S. Pat. No. 5,741,327 (stent with markers) and Lorenzo, U.S. Pat. No. 5,836,892 (guidewires with markers). In techniques using medical imaging devices, images are taken to observe the stents, but these images are typically still images that show only the final positions of the stents or guidewires or balloons after placement.

Various image processing techniques have been proposed and are generally applicable to enhance angiographic images. For example, background subtraction attempts to separate the coronary arteries from patient background structures. But background structures can cause tracking errors or densitometric errors in correctly tracked arteries, since background structures are superposed on the vessel in the images. In the absence of motion, digital subtraction of a mask image taken before the contrast injection may be performed to remove the background structures, but this method has not been clinically successful because of involuntary patient motion. Motion-correction in current clinical DSA (digital subtraction angiography) systems is accomplished by a manually controlled translation of the mask image with respect to the contrast image. Unfortunately, since cardiac motion is more complex then simple translations, this technique will reduce artifacts in some parts of the image but reinforce or create artifacts in other parts of the image. Other methods to improve accuracy have been proposed, including a system for automatic re-masking during image acquisition, in which a new mask is selected whenever a similarity measure drops below a certain threshold, and a system using control points to determine the motion between the mask and live images. Manual selection of control points, however, can introduce errors if the points are not corresponding between the pre-processed and the mask images. Another technique, known as flexible mask subtraction, automatically tracks features from the mask to the live image. This method requires prior segmentation of the vessel from the surrounding background; as a result, regions beneath the vessel are not tracked directly but are interpolated. In general, a 2 D warped mask subtraction method involves subtraction of a previously acquired image that has been warped to correct for motion (E. H. W. Meijering et al., "Retrospective motion correction in digital subtraction angiography: A review," *IEEE Trans. Med. Imag.*, vol. 18, No. 1, pp. 2–21, 1999).

All of the above-mentioned background subtraction techniques suffer from several important limitations. First, they use a "mask" image of the background taken prior to stent deployment. The long delay between acquisition of the mask image and the image with stents present makes involuntary patient motion (such as breathing) a major source of degradation. Second, the subtraction of two images containing random noise results in an image with more noise than the original images. Third, the three-dimensional background motion is modeled as a single two dimensional motion. Only the portion of the background which moves according to the estimated two-dimensional motion mapping is correctly subtracted.

One method for reducing random noise in moving images is motion-compensated temporal averaging (e.g. Dubois E, Sabri S, "Noise Reduction in Image Sequences Using Motion-Compensated Temporal Filtering", *IEEE Trans. Comm.* 32(7):826–831, 1984). A feature such as a stent can be tracked and shifted to a common position in each image prior to temporal averaging. However, in projection images such as angiograms the presence of background structures can cause tracking errors which blur the time-averaged image.

The method of moving layer decomposition was developed in order to improve the accuracy of quantitative measurements made from coronary angiograms (QCA). This technique performs tracking and motion-compensated temporal averaging of different image structures (layers) to achieve both background removal and noise reduction. However, in fluoroscopic images of deployed stents the stent signal is usually too weak to track accurately. In angiographic image sequences containing opacified arteries, tracking errors can result from the overlapping vessel and background structures.

In summary, prior methods for enhancement of angiographic images are inadequate to assist stent deployment. Background subtraction techniques increase random noise which degrades stent visibility and quantitative measurements of lumen shape. Tracking techniques suffer from errors due to the presence of background structures and the faintness of the stent in the images.

SUMMARY OF THE INVENTION

In view of the prevalent use of stenting in coronary interventions, the adequacy of angiographic guidance and evaluation of stent deployment needs to be improved.

Accordingly, the present invention is directed to a method for improving coronary stent deployment by applying a multiframe analysis that substantially diminishes one or more of the problems due to limitations and disadvantages of the related art.

An object of the present invention is to provide a method to improve clinical visualization of stents during and following deployment.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims hereof as well as the appended drawings.

According to the present invention, radiopaque markers on the delivery balloon, guidewire, or other device are used to provide a trackable feature that is co-moving with the stented vessel. Placement of a marked device into a vessel lumen enables one to enhance the visibility not only of the marked device, but also of any previously deployed stents nearby in the same vessel. A cine x-ray (fluoroscopic) image sequence is acquired while the radiopaque markers are inside the stented lumen. Enhanced images of the stents are produced by layer decomposition of the fluoroscopic image sequence. This decomposition into moving layers is performed by tracking image features and performing motion-compensated temporal averaging of background and stent features.

In another aspect, the present invention provides a method for accurate deployment of coronary stents with no overlap or gap between multiple stents. Accurate positioning of an additional stent is obtained by repeated adjustment and assessment of the relative positions of the deployed and undeployed stents using enhanced fluoroscopic images obtained by the procedure described above.

In another aspect, the present invention provides a method to improve assessment of stent dilation. In this case the vessel is filled with a contrast agent during imaging. Layer decomposition is performed in order to yield background-subtracted and time-averaged images of the layer containing the opacified vessel lumen. In order to improve tracking accuracy, the time-average of the image sequence (stationary background layer) is subtracted prior to tracking the vessel. In addition, the stented region is outlined and isolated from the rest of the image for use as a kernel for vessel tracking. The resulting vessel layer image can then be used to assess adequacy of stent expansion by visual or quantitative assessment of the relative amount of lumen narrowing or broadening in the stented region (e.g. percent diameter stenosis, densitometric area stenosis, or volumetric density deficit index described by Rozenman). If the stent is assessed to be insufficiently dilated, additional balloon inflations can be performed.

It is to be understood that both the foregoing general description and the following detailed description are exemplary and explanatory and are intended to provide further explanation of the invention as claimed.

DETAILED DESCRIPTION OF THE PREFERRED EMBODIMENTS

Figure 1:
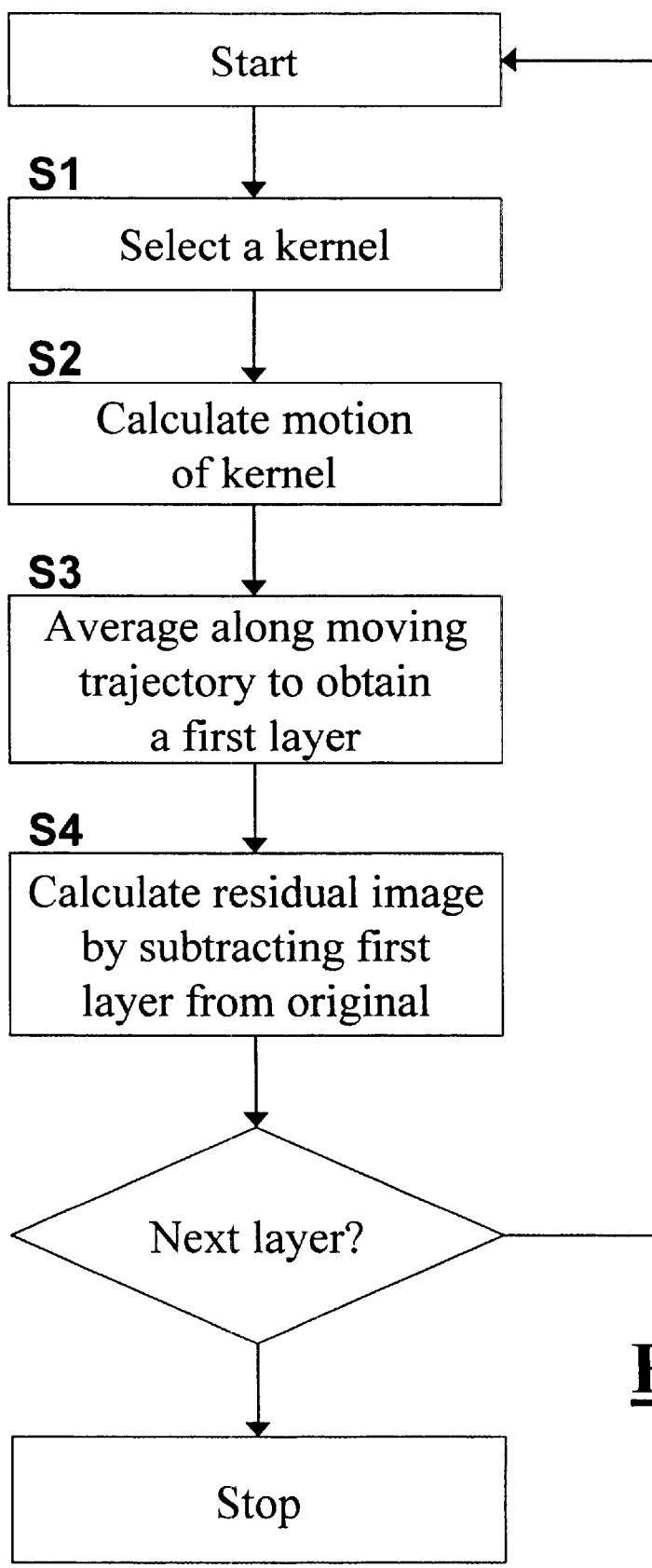
FIG. 1 is a flow chart illustrating an image processing method according to an embodiment of the present invention.

The present invention is based on two techniques, namely, an image processing method known as "moving layer decomposition", and coronary stent deployment methods using marked delivery guidewires or balloons. Moving layer decomposition is an image processing method for analyzing a time-series of images, such as coronary angiograms, to obtain an image of the object of interest with clearer signals and lower noises. The method focuses on an identifiable feature in the angiograms (a "layer"), such as a coronary vessel, that moves or rotates with respect to a background across a series of images. It tracks the motion of the feature, and averages the image intensity of the feature using several images of the time-series taking into account the movement of the feature. In the resulting enhanced image, the feature is more clearly visible.

A method for decomposing coronary angiograms into non-rigid moving layers undergoing translation, rotation and scaling is described in an article by R. A. Close and J. S. Whiting, *Medical Imaging* 1999: *Image Processing*, K. M. Hanson, Editor, *Proc. SPIE* 3661, pp. 1515–1520, 1999 ("the Close and Whiting article"), and summarized below.

First, the optical density of an image P(x, y, t) is modeled as a sum of moving layers as follows:

$$u_L(x, y, t) = (u_L(x, y, t), v_L(x, y, t))$$

$$P(x, y, t) = \sum_L \rho_L(x - u_L(x, y, t), y - v_L(x, y, t)) \quad (1)$$

where t is time and the layers $\rho_L$ are defined by their density at t=0. The motion of each layer ($u_L$(x, y, t), $v_L$ (x, y, t) ) is computed to be a motion from the current position to the position at time t=0 so that moving averages of the layer densities are easily performed. In other words, the motion is a mapping of the layer from the position at t=0 to the current position.

Phase correlation is useful for measuring pure translations with arbitrarily large displacements. Simple correlation typically peaks at the true displacement but has multiple peaks at nearby displacements. Phase correlation, on the other hand, ideally yields a delta-function at the true displacement. The phase correlation $\Phi(k_x, k_y, t_i, t_j)$ between two images $I(k_x, k_y, t_i)$ and $I(k_x, k_y, t_j)$ in the spatial frequency domain $(k_x, k_y)$ is:

$$\Phi(k_x, k_y, t_i, t_j) = \sum_{k_x, k_y} \frac{I(k_x, k_y, t_i) I(k_x, k_y, t_j)}{(|I(k_x, k_y, t_i)|^2 |I(k_x, k_y, t_j)|^2)^{1/2}} \quad (2)$$

One method for computing rotation and scaling is by using autocorrelations of sequential images. The autocorrelation is independent of translation. Rotation and scaling (r'=ar, θ'=θ+φ, where r, θ and φ are coordinates of a polar system) form a pure displacement in the log-polar coordinates because ln r'=ln r+ln a, θ'=θ+φ. Autocorrelation, however, is not directly suitable for multiple layers because autocorrelation is a nonlinear function of the data.

A preferable method for computing translation, rotation and scaling is by using blurred images. Since blurring is a linear operation, the model of each image as a superposition of layers is preserved. The blurred images are obtained by averaging over allowable rotations and scales. Translation is obtained by computing the phase correlation of the resultant blurred images. The actual rotation and scaling is then obtained after compensating for translation. Specifically, the first image of the sequence is used as a kernel, and a weighted correlation with each successive image is computed. Rather than a pure phase correlation, a weighted correlation function $C_W$ is computed, which is weighted inversely by a Wiener-like filter composed of the estimated image power spectrum $P_1$ plus an estimate of the noise power PA,.

$$C_W(k_x, k_y, t_i, t_j) = \frac{I(k_x, k_y, t_i) I(k_x, k_y, t_j)}{P_I(k_x, k_y) + P_N(k_x, k_y)} \quad (3)$$

The image and noise power spectra are estimated from the mean and variance, respectively, of the power spectra of the separate frames. This expression for weighted correlation reduces to the phase correlation in the special case of a noise-free single moving layer. The maximum of the weighted correlation is taken to be the correct translation (or rotation and scaling when applied to the log-polar images).

Once the motion of a layer is estimated, the layer density is estimated by averaging along the moving trajectories. The uniform component of each layer is not determined. Each time a new layer density is computed by moving average, its density is subtracted from the corresponding position in each of the previously computed layers. After all layer motions have been found, the density estimates may be improved by using a conjugate gradient technique.

In the method described in the Close and Whiting article, the coronary vessels to be visualized are used as the first layer. The article describes processing angiographic sequences to yield enhanced image of coronary vessels, but the technique has never been applied to stent deployment.

The present invention provides a method for precisely evaluating coronary stent deployment by marking the stent guidewire or delivery balloons using radiopaque marker, and tracking the image of the stent using the moving layer decomposition technique. Although the stent itself is typically not clearly visible, it co-moves with the markers. Thus, by tracking the movements of the markers and performing time averaging based on the tracking, the visibility of the stent or stented lumen can be enhanced. One may also use the method to enhance the visibility of various other devices inserted within a coronary vessel to treat or evaluate a patient, including, for example, an ultrasound imaging device and an atherectomy catheter.

In one embodiment of the present invention, a stent to be placed in a patient's coronary vessel is attached to delivery guidewires and balloons. The guidewires and/or balloons are provided with radiopaque markers using known methods such as described in Lorenzo, U.S. Pat. No. 5,836,892 or using any other suitable methods. The marker may be either a radiopaque material coated on or used as the material for the guidewire or balloon, or they may be separate marker elements attached to the guidewire or balloon. The term "markers" and "marked guidewires or balloons" are used interchangeably to cover both configurations. The stent is then placed into the patient's coronary vessel using any suitable technique, and x-ray cine image sequences (or time-series images) are acquired during stent placement. In the time-series images (or frames), radiopaque markers on the guidewires and/or balloons will be clearly visible, although the stents and blood vessels are typically not.

A method for processing the time-series images according to an embodiment of the present invention is described with references to FIG. 1. First (Step S1), a reference image (or kernel) is selected, which may be one of the frames, a feature extracted from one of the frames, or a model of a feature known to be present in the frames, such as a marker. Preferably, the marker is used as the kernel. Then (Step S2), the optimal motion which best maps the kernel to each frame is calculated. Phase correlation and image blurring techniques described above are preferably use to compute translation rotation and scaling, although other suitable methods may also be used. Then (Step S3), the average image density (or gray level) along the moving trajectory is computed using the estimated motion for each point in the kernel. This moving average is an estimate of the first layer. If a feature including the marker is used as the kernel, the stent will be visible in the first layer because the stent co-moves with the marker. Subsequently (Step S4), a residual image sequence is computed by subtracting the moving first layer from each image in the time-series images. Then, the steps S1–S4 are repeated with a new kernel. The new kernel is selected from the residual image sequence in a similar way as the selection of the first kernel. As each new layer density is computed, previous layer density estimates may be improved by subtracting the density of the new layer, taking into account any relative movement between the two layers.

In the above method, one of the layers may be forced to have zero motion, especially a layer that may not be accurately reproduced by tracking. For example, in images of non-opacified arteries containing a moving guidewire, forcing the first computed layer to have zero motion generates a stationary background layer which can be subtracted prior to tracking the guidewire. This procedure can reduce tracking errors which might otherwise be caused by background structures.

As a result of the above processing, each layer represents a motion-compensated temporal-average of a certain structure (such as stent or guidewire) with other layers subtracted away. This image is referred to as "time-averaged DSA". By adding the final residual image to the vessel layer or the guidewire layer, a tracked sequence with background structures subtracted but without temporal averaging is obtained. This is referred to as "tracked DSA sequence".

These images can then be used to visualize the stents or stented vessels to optimize stent deployment, such as to assess residual stenosis of a stented lumen, to assess uniformity of stent expansion, or to assist in placement of multiple stents with no overlaps or gaps. To ensure proper dilation of an individual stent, the cardiologist performing the procedure must determine that the stent is uniformly expanded and that the size of the stented lumen is equal to or slightly larger than the natural size of the lumen. To assess lumen size, an angiographic sequence is acquired with an injected contrast agent to opacify the artery. Layer decomposition is then performed as described above. Using the tracked DSA sequence and the time-averaged DSA images, it may be visually determined whether the lumen bulges outward in the stented region. A quantitative measure of residual stenosis may be computed densitometrically using, for example, methods described in the Rozenman et al. article mentioned earlier. In practice, part of the stent may be fully expanded but sometimes other parts may not be fully expanded. This situation is typically difficult to assess from angiographic images with opacified vessels. To assess uniformity of expansion, layer decomposition may be performed on a contrast-free image sequence containing a marked guidewire or balloon in the vicinity of the deployed stent. Since the guidewire moves with the stented vessel, the associated layer will contain the stent, and uniformity of expansion may be assessed from this layer. Visibility of the stent image on a display device (such as a monitor) may be further improved by applying known image processing techniques (e.g. histogram equalization to enhance low-contrast features, window and level to enhance contrast within a specific range of gray levels, etc.). Using this method, if the stent is determined to be partially or fully under-expanded, additional balloon inflation may be performed until proper expansion is achieved.

For proper placement of multiple stents, the cardiologist must determine the relative positions of the previously deployed stent and the guidewire or deployment balloon holding the new stent. To accomplish this, layer decomposition may be applied to an image sequence containing the marked guidewire or balloon near the previously deployed stent. Because the previously deployed stent and the newly inserted device are both moving with the coronary artery which surrounds them, they will be visible in the same layer image. The cardiologist may then adjust the position of the deployment balloon until the new stent is properly adjacent to the previously deployed stent.

The moving layer decomposition technique has several advantages over 2 D warped mask subtraction. First, a mask image with stent-free background is not necessary for moving layer decomposition. If a mask image is present, it can be used as a layer in layer decomposition. Layer decomposition can be satisfactorily applied even when the relative motion between background and the stent is small. Second, in layer decomposition, since the background layers are computed by averaging over multiple frames (i.e., motion-compensated temporal filtering), they are less degraded by random noise than a single mask image. A typical mask-subtracted DSA image, on the other hand, has twice the random noise of the live image. Third, layer decomposition treats the background as multiple two-dimensional layers undergoing independent spatial transformations rather than as a single two-dimensional structure. This allows subtraction of all background structures that are not co-moving with the stent or stented vessel segment. With single-layer mask images, only the portion of the background that moves according to an estimated two-dimensional motion mapping is correctly subtracted.

In summary, the present invention takes advantage of the marked delivery guidewires or balloons, and applies the moving layer decomposition technique to track the movements of the clearly visible radiopaque markers. In the present invention, although the object of interest (the stent) is not tracked, an enhanced image of the stent is obtained because the stent has a fixed spatial relationship with respect to the markers which are tracked. Further, although artificial radiopaque markers have been used in other image processing methods to enhance an image feature of interest other than the marker, the method has never been used in combination with moving layer decomposition. In addition, the technique of moving layer decomposition can be applied to images of the opacified lumen following stent deployment in order to improve the assessment of stent dilation. For this purpose the tracking of the vessel is improved by prior subtraction of the time-averaged image sequence.

Figure 2:
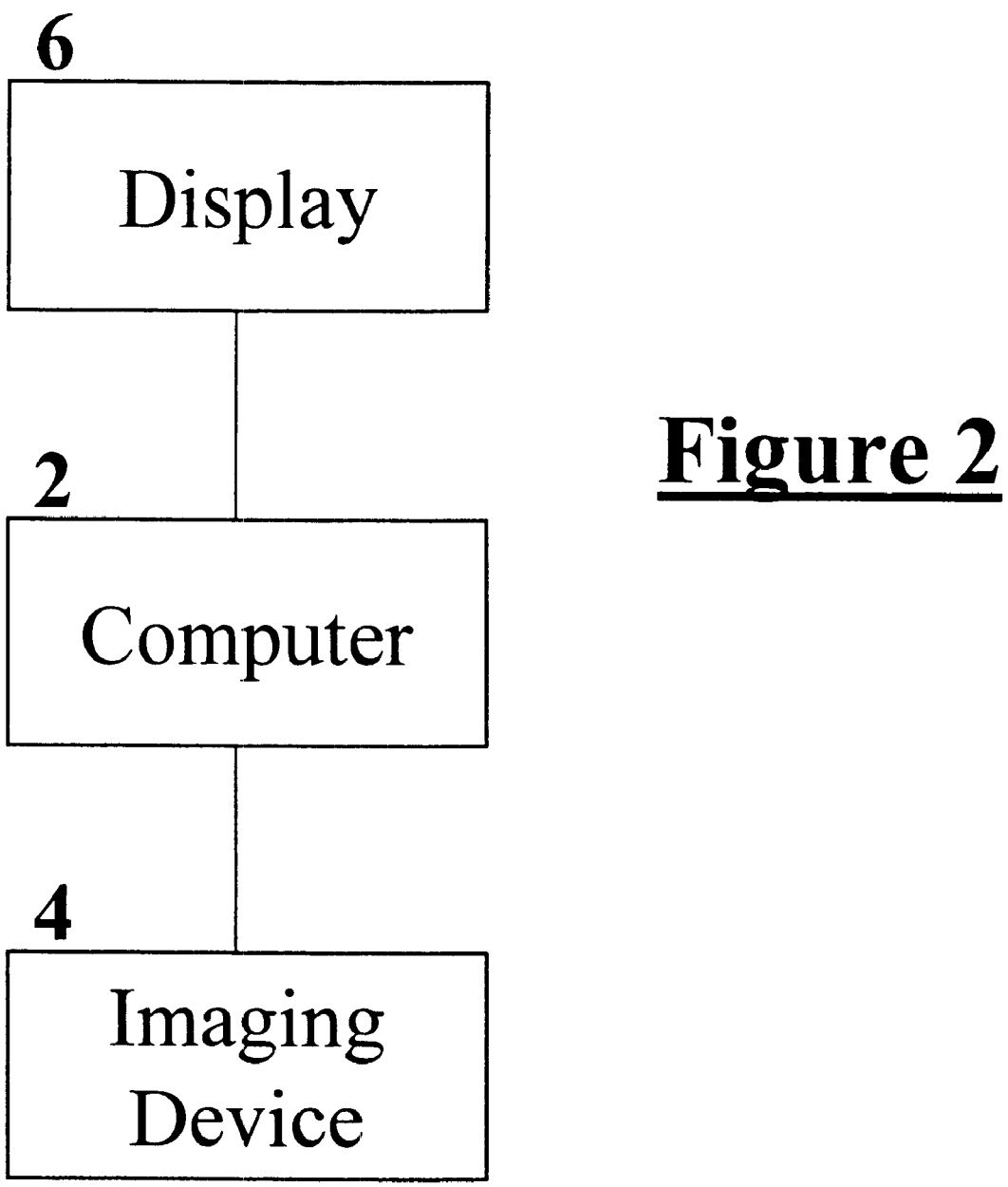
FIG. 2 illustrates an imaging system in which the present invention may be applied.

The image processing methods embodying to the present invention may be carried out using a programmed computer system configured to receive image data from a medical imaging device, such as an image intensifier fluoroscope or cesium iodine/amorphous silicon flat panel detector system. The computer system may simultaneously perform the control of the imaging device. FIG. 2 illustrates the configuration of such system including a computer 2, an imaging device 4 and a display 6.

It will be apparent to those skilled in the art that various modifications and variations can be made in an image processing method according to the present invention without departing from the spirit or scope of the inventions. Thus, it is intended that the present invention cover modifications and variations of this invention that come within the scope of the appended claims and their equivalents.

What is claimed is:

1. A method for generating a visual image of a lumen of a coronary vessel and a device moving within the vessel, the method comprising:

inserting radiopaque material into the vessel;

obtaining a time series of images containing the vessel; and decomposing the time series of images into a sum of multiple moving layers wherein decomposing the time-series of images comprises selecting a reference image from an image frame within a first time-series of images;

calculating from the first time-series of images a first motion function which maps each image to the reference image;

calculating, by applying the first motion function for each image, a first layer image which is a time-average of the images moved into alignment with the reference image;

generating a sequence of residual images by subtracting the first layer image from each image of the original sequence;

calculating subsequent layer images by repeating the steps of selecting a reference image, calculating a motion function, calculating a layer image, and generating a sequence of residual images.

2. The method of claim 1, wherein the device is selected from the group consisting of a stent, a catheter, a guidewire, an endoscope, an angioplasty balloon, an atherectomy cutting device, and an intravascular ultrasound device.

3. The method of claim 1, wherein the radiopaque material comprises at least one marker attached to the device.

4. The method of claim 1, wherein the radiopaque material comprises a liquid contrast agent injected into the vessel.

5. The method of claim 1, wherein the method of decomposing the time-series of images further comprises refining a layer image calculation by subtracting from the layer image:

a sequence formed from a subsequent layer image attenuated by dividing the number of images in the sequence moving with the difference between two layer motions for each time interval.

6. The method of claim 1, wherein at least one motion function is set to zero.

7. The method of claim 1, wherein at least one motion function is calculated using phase correlation.

8. The method of claim 1, wherein at least one motion function is calculated using blurred images.

9. The method of claim 1, further comprising using an image intensifier fluoroscope to obtain the time series of images.

10. The method of claim 1, further comprising displaying layer-derived digital subtraction angiography and time-averaged digital subtraction angiography images on a display.

11. A method for positioning at least one stent within a coronary vessel, the method comprising:

inserting, with a delivery device, at least one stent into a coronary vessel, wherein the delivery device has at least one radiopaque marker;

obtaining a time series of images containing the vessel;

decomposing the time series of images into a sum of multiple moving layers;

displaying, on a display, images selected from the group consisting of layer-derived digital subtraction angiography images and time-averaged digital subtraction angiography images;

positioning the at least one stent within the vessel wherein decomposing the time-series of images comprises selecting a reference image from an image frame within a first time-series of images;

calculating from the first time-series of images a first motion function which maps each image to the reference image; calculating, by applying the first motion function for each image, a first layer image which is a time-average of the images moved into alignment with the reference image;

generating a sequence of residual images by subtracting the first layer image from each image of the original sequence;

calculating subsequent layer images by repeating the steps of selecting a reference image, calculating a motion function, calculating a layer image, and generating a sequence of residual images.

12. The method of claim 11, further comprising the step of determining, by visually inspecting the display, the proper position of the at least one stent.

13. The method of claim 11, wherein the step of positioning the at least one stent within the vessel further comprises positioning a first stent adjacent to a second stent such that there is no overlap and no gap between the first and second stents.

14. The method of claim 11, wherein the delivery device is selected from the group consisting of a guidewire, a catheter, and an angioplasty balloon.

15. The method of claim 11, further comprising injecting a liquid contrast agent into the vessel.

16. The method of claim 11, further comprising using an image intensifier fluoroscope to obtain the time series of images.

17. The method of claim 11, wherein the method of decomposing the time-series of images further comprises refining a layer image calculation by subtracting from the layer image:

a sequence formed from a subsequent layer image attenuated by dividing the number of images in the sequence moving with the difference between two layer motions for each time interval.

18. The method of claim 11, wherein at least one motion function is set to zero.

19. The method of claim 11, wherein at least one motion function is calculated using phase correlation.

20. The method of claim 11, wherein at least one motion function is calculated using blurred images.

* * * * *

UNITED STATES PATENT AND TRADEMARK OFFICE
CERTIFICATE OF CORRECTION

| | | |
|---|---|---|
| PATENT NO. | : 6,532,380 B1 | Page 1 of 1 |
| APPLICATION NO. | : 09/608392 | |
| DATED | : March 11, 2003 | |
| INVENTOR(S) | : Robert A. Close et al. | |

It is certified that error appears in the above-identified patent and that said Letters Patent is hereby corrected as shown below:

Beginning at column 1, under the title, Line 3; please insert the following:

--GOVERNMENT LICENSE RIGHTS

The U.S. Government has a paid-up license in this invention and the right in limited circumstances to require the patent owner to license others on reasonable terms as provided for by the terms of Grant No. 5R01HL053455-03 awarded by the National Institutes of Health.--

Signed and Sealed this

Thirteenth Day of April, 2010

David J. Kappos
*Director of the United States Patent and Trademark Office*